United States Patent
Tsuchiya et al.

(10) Patent No.: US 8,253,108 B2
(45) Date of Patent: Aug. 28, 2012

(54) RADIATION IMAGING SYSTEM, NUCLEAR MEDICINE DIAGNOSIS APPARATUS AND POSITIONING ADJUSTING MECHANISM

(75) Inventors: Katsutoshi Tsuchiya, Hitachi (JP); Takafumi Ishitsu, Hitachi (JP); Tsuneaki Kawaguchi, Kashiwa (JP)

(73) Assignee: Hitachi, Ltd., Tokyo (JP)

( * ) Notice: Subject to any disclaimer, the term of this patent is extended or adjusted under 35 U.S.C. 154(b) by 506 days.

(21) Appl. No.: 12/342,805

(22) Filed: Dec. 23, 2008

(65) Prior Publication Data

US 2009/0166541 A1    Jul. 2, 2009

(30) Foreign Application Priority Data

Dec. 28, 2007   (JP) ................. 2007-340841

(51) Int. Cl.
    *G01T 1/166* (2006.01)
(52) U.S. Cl. ................................. 250/363.05
(58) Field of Classification Search ........... 250/363.04, 250/363.05, 363.1, 394
See application file for complete search history.

(56) References Cited

U.S. PATENT DOCUMENTS

| | | | |
|---|---|---|---|
| 6,157,700 A | 12/2000 | Sako | |
| 7,262,415 B2 | 8/2007 | Crosetto | |
| 2002/0003413 A1 | 1/2002 | Chiba | |
| 2007/0029495 A1 | 2/2007 | Petrillo et al. | |

FOREIGN PATENT DOCUMENTS

| | | |
|---|---|---|
| EP | 1 298 456 A1 | 4/2003 |
| JP | 2001-324569 | 11/2001 |
| JP | 2006-119113 | 5/2006 |

*Primary Examiner* — Mark R Gaworecki
(74) *Attorney, Agent, or Firm* — Mattingly & Malur, PC

(57) ABSTRACT

A radiation imaging system includes a detecting unit including a plurality of radiation detecting elements arranged in a plane for radiation detection, a collimator provided with through holes respectively aligned with the radiation detecting elements and opening in an entrance surface such that radiation from a specified direction is selectively made to fall on the radiation detecting elements. A second case joined to a first case fixed to the side surface of the collimator defines a holding chamber G, and a holder holding the detecting unit is placed in the holding chamber G such that spaces that allow the holder to be moved in a plane parallel to the entrance surface are formed between the holder and the second case. A position adjusting mechanism for adjusting the positional relation between the second case and the holder by moving the holder relative to the second case.

5 Claims, 5 Drawing Sheets

RADIATION IMAGING SYSTEM, NUCLEAR MEDICINE DIAGNOSIS APPARATUS AND POSITIONING ADJUSTING MECHANISM

BACKGROUND OF THE INVENTION

1. Field of the Invention

The present invention relates to a radiation imaging system which takes in incident radiation distribution and a nuclear medicine diagnosis instrument therefore. More particularly, the present invention relates to a technique for achieving accurate diagnosis.

2. Description of the Related Art

A diagnostic method using a single photon emission computed tomography system (abbreviated to "SPECT instrument"), among nuclear medicine diagnosis instruments using radiations for medical diagnosis, gives a radioactive medicine to a subject, namely, a patient, measures the distribution of the radioactive medicine in the subject's body by using images projected on a plurality of planes at different angles and produces a tomographic picture from those images. This method can detect functions on the level of molecules and metabolism and can provide a tomographic picture based on physical functions.

The SPECT brings a plurality of radiation imaging devices from predetermined directions near to a predetermined part of the subject, such as the heart or the head, revolves the radiation imaging devices about the body axis of the subject to obtain minute information about a specific organ and a specific function. High-order diagnosis can be made on the basis of the thus obtained minute information.

It is desired to produce a picture of a high picture quality (high resolution) to achieve advanced diagnosis accurately. Since the closer the radiation imaging devices to the subject, the higher is the resolution, it is desired to diminish a space surrounding the effective field of view of each radiation imaging device to dispose a plurality of radiation detecting surfaces close to the subject.

The following measures are taken to improve image quality by improving spatial resolution. A pixel detector is employed for such a purpose. The pixel detector has a detecting unit formed by integrating a plurality of radiation detecting elements capable of detecting pixels of a picture projected on a plane in a high density. This pixel detector improves intrinsic spatial resolution. Resolution can be remarkably improved particularly in closer imaging. Use of the pixel detector diminishes a space needed by a photomultiplier tube extending outside the detecting surface (effective field of view) because a signal read system can be disposed on the back surface of the detecting surface (effective field of view).

A collimator is mounted in front of the detecting surface. The collimator regulates incident directions from which radioactive rays radiated from the subject and falling from different directions on the detecting unit. The collimator of the pixel detector needs to be provided with a plurality of through holes determining the incident directions of radioactive rays at positions coinciding with the radiation detecting elements. As mentioned in JP-A 2006-119113, a moiré pattern is produced in a projected picture if the through holes are dislocated from their correct positions.

A method of correcting the incorrect positional relation between the through holes and the radiation detecting elements mentioned in JP-A 2001-324569 adjusts the position of the collimator relative to a box holding the detecting unit by an adjusting screw.

The incorrect positional relation between the through holes and the radiation detecting elements causes not only formation of a moiré pattern, but also the deterioration of resolution and the reduction of linearity of a picture. Accuracy of the positional relation between the through holes and the radiation detecting elements needed to ensure the linearity of the picture is still higher than that needed to solve the problem of a moiré pattern.

In a detecting unit for obtaining a tomographic picture of high resolution, radiation detecting elements are arranged at pitches in the range of about 1 to 2 mm. Under such a condition, an allowable error in the positions of the through holes relative to the corresponding radiation detecting elements needed to avoid the foregoing problems is in a narrow range of 0.1 to 0.2 mm.

If the pixel density is increased by reducing the size of pixels to elevate the accuracy of diagnosis, the collimator needs to be installed in a high mechanical accuracy.

The box holding the detecting unit of a radiation imaging system using radiations, such as γ-rays, for obtaining an image is required to have a radiation screening function also. Therefore the radiation imaging system often has a large size and a large weight.

When machining accuracy is taken into consideration, it is difficult to confine positional errors of the component parts of the radiation imaging system to the foregoing range of allowable errors. Such errors in the position of the component parts may be reduced by a position adjusting means for adjusting the positional relation between the detecting unit and the collimator after installation.

When the radiation imaging system is provided with a position adjusting means for adjusting the position of the heavy collimator, the radiation imaging system needs a large, heavy, movable mechanism, the detector box is practically enlarged and the merits of closer imaging are nullified.

SUMMARY OF THE INVENTION

The present invention has been made to solve the foregoing problems and it is therefore an object of the present invention to provide a radiation imaging system provided with a position adjusting means for adjusting the positional relation between a detecting unit and a collimator and realizing reducing an outside space of an imaging field of view to enable closer imaging to an object, and a nuclear medicine diagnosis instrument capable of accurately achieving advanced diagnosis on the basis of a functional image.

One aspect of the present invention is directed to a radiation imaging system including: a detecting unit provided with a plurality of radiation detecting elements arranged in a plane for radiation detection; a collimator provided with through holes respectively aligned with the radiation detecting elements and opening in an entrance surface such that radiations from a specified direction are selectively made to fall on the radiation detecting elements; a second case joined to a first case fixed to the side surface of the collimator to define a holding chamber; a holder holding the detecting unit and placed in the holding chamber such that spaces that allow the holder to be moved in a plane parallel to the entrance surface are formed between the holder and the second case; and a position adjusting means for adjusting the positional relation between the second case and the holder by moving the holder relative to the second case in distance ranges defined by the spaces.

In the radiation imaging system thus constructed, the collimator is fixed to the first and the second case, and the detecting unit is displaced relative to the collimator for positional adjustment. The position adjusting means that moves the detecting unit relative to the collimator is disposed on the back side opposite the side of the entrance surface. Therefore, the position adjusting means does not contribute substantially to enlarging a space needed to install the radiation imaging system.

A nuclear medicine diagnosis instrument provided with the radiation imaging system has an imaging field of view extending near to the radiation imaging system. Therefore, the radiation imaging system can be moved close to the subject to without being interfered with by the shoulders, the arms and the chin to obtain an image.

The position adjusting mechanism includes a holder bottom wall provided with guide grooves, and one or more eccentric cams. The holder bottom wall has a sliding contact with the second case and the eccentric cams are held at the second case. The guide grooves extend respectively in a first longitudinal direction and a second longitudinal direction perpendicular to the first longitudinal direction. The eccentric cams are loosely engaged respectively in the guide grooves extending in the first and second longitudinal directions in the holder. The holder is displaced in the second longitudinal direction when the eccentric cam engaged in the guide groove extending in the first longitudinal direction is turned, and the holder is displaced in the first longitudinal direction when the eccentric cam engaged in the guide groove extending in the second longitudinal direction is turned.

The position of the detecting unit relative to the collimator with respect to directions respectively parallel to an x-axis and a y-axis, and a turning direction θ can be adjusted. Thus the positional relation between the detecting unit integrated in a high degree of integration to increase pixel density and the collimator can be precisely adjusted.

According to the aspect of the present invention, there is provided the radiation imaging system provided with the position adjusting means for adjusting the positional relation between the detecting unit and the collimator and capable of narrowing the space outside the imaging field of view to achieve closer imaging, and the nuclear medicine diagnosis instrument capable of accurately achieving advanced diagnosis.

BRIEF DESCRIPTION OF THE DRAWINGS

The above and other objects, features and advantages of the present invention will become apparent from the following description taken in connection with the accompanying drawings, in which.

DESCRIPTION OF THE PREFERRED EMBODIMENTS

Preferred embodiments of the present invention will be described with reference to the accompanying drawings.

Figure 1:
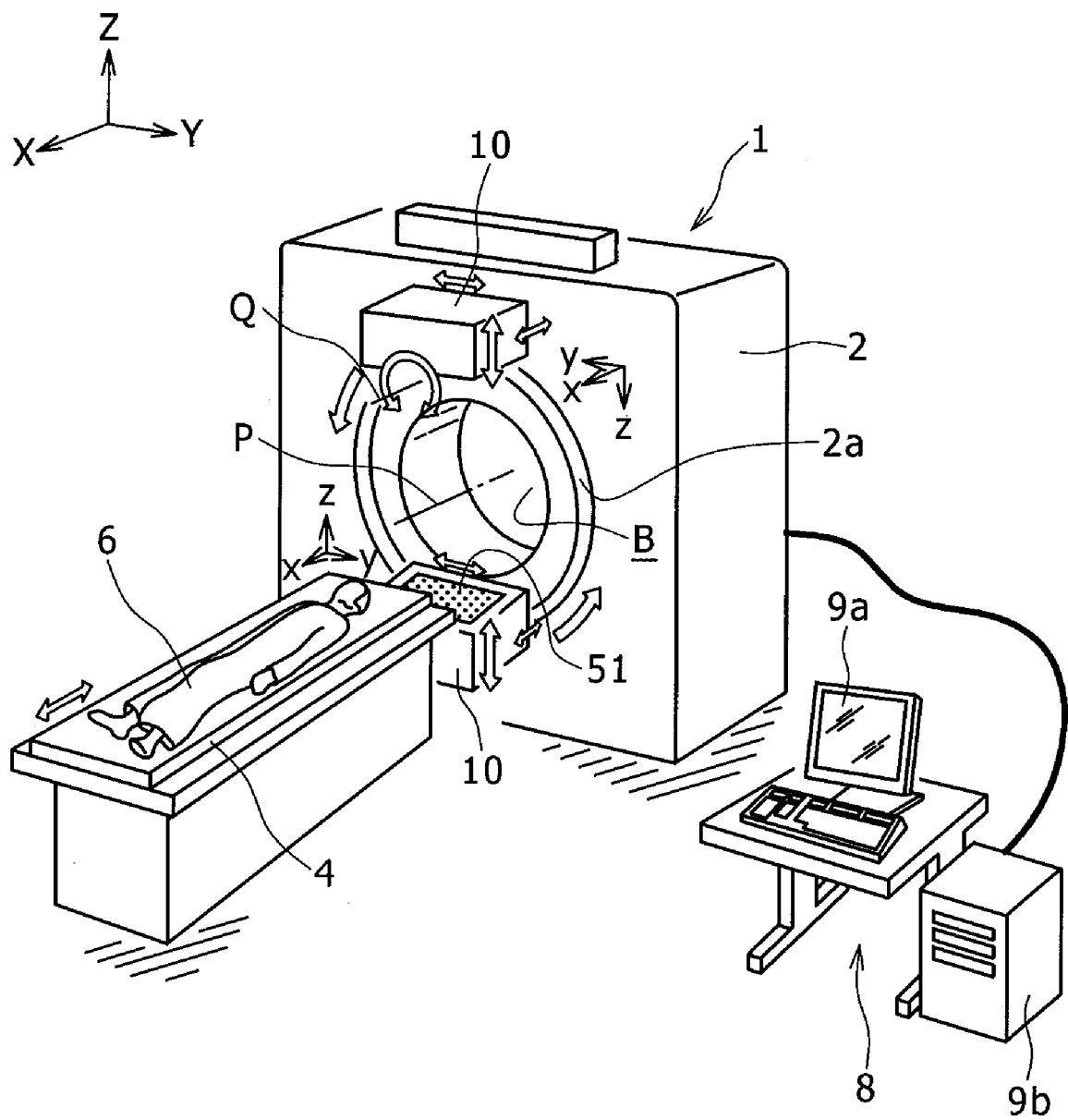
FIG. 1 is a perspective view of a nuclear medicine diagnosis instrument in a preferred embodiment according to the present invention.

Referring to FIG. 1, a nuclear diagnosis instrument 1 in a preferred embodiment according to the present invention includes two radiation imaging systems 10, a gantry (supporting means) 2 supporting the radiation imaging systems 10 so as to be movable in a space, a bed 4 on which a subject 6 who has taken a radioactive medicine is laid down, and an image processing system 8 for processing signals provided by the radiation imaging systems 10.

A tomographic picture based on the physical functions of the subject 6 is displayed on a display 9a for medical diagnosis.

In the following description, a space having a reference point on the nuclear diagnosis instrument will be defined by an XYZ-coordinate system having its origin on the nuclear diagnosis instrument 1 and a space having a reference point on the radiation imaging system 10 will be defined by a xyz-coordinate system having its origin on the radiation imaging system 10.

The bed 4 can support the subject 6 at an optional position in the space defined by the XYZ-coordinate system with the body axis of the subject 6 extended in an optional direction. The radioactive medicine given to the subject 6 contains, for example, Tc-99 m having a radioactive half-life of 6 h. The bed 4 holds the subject 6 at a predetermined position in a predetermined direction such that the radiation imaging system 10 can easily detect γ-rays emitted from the subject 6.

The gantry 2 can fixedly hold each radiation imaging system 10 at an optional position in the space defined by the XYZ-coordinate system with the entrance 51 of the radiation imaging system 10 faced in an optional direction. A bore B is formed in a central part of the gantry 2. Part of the subject 6 excluding an objective part of the subject 6 is received in the bore B to separate the part of the subject 6 from the field of view of the radiation imaging system 10 during an imaging operation.

A first drive device, not shown, is disposed in the gantry 2. The first moving device drives each radiation imaging system 10 for revolution along a revolution path 2a surrounding the bore B about a revolution axis P in the space defined by the XYZ-coordinate system.

The first drive device fixes the radiation imaging device 10 through a second drive device, not shown. The second drive device can drive the radiation imaging system 10 for rotation about a rotation axis Q in the space defined by the XYZ-coordinate system and for movement along the X-axis, the Y-axis and the Z-axis. Thus, the radiation imaging system 10 can be fixedly located at an optional position with the entrance surface 51 faced in an optional direction in the space defined by the XYZ-coordinate system.

Although only the rotation axis Q parallel to the X-axis is shown in FIG. 1, the rotation axis Q is parallel to an axis perpendicular to the X-axis in some cases.

The radiation imaging system 10 can be brought close to an objective part of the subject 6 and the entrance surface 51 can be disposed opposite to the objective part of the subject 6 by operating the bed 4 and the gantry 2.

Although the nuclear diagnosis instrument 1 shown in FIG. 1 is provided with the two radiation imaging systems 10, the present invention is. not limited thereto in its practical application. The nuclear diagnosis instrument 1 may be provided with one radiation imaging system 10 or three or more radiation imaging systems 10. Two radiation imaging systems 10 among a plurality of radiation imaging systems 10 can be disposed so that their entrance surfaces 51 at an angle of 90° to each other without mechanically interfering with each other or can be disposed so that their entrance surface 51 are contained in a plane.

The image processing system 8 includes the display 9a and a data processing unit 9b. The data processing unit 9b processes measured data on the distribution of intensities of radioactive rays on the entrance surface 51 of the radiation imaging system 10 and a position signal conveying the position of the radiation imaging system 10, namely, a signal conveying the coordinates of the position of the radiation imaging system 10 in the XYZ-coordinate system, provided by the gantry 2 to produce an image of a section of the subject 6.

The image processing system 8 displays a picture of the section of the subject 6 projected on a plane by the display 9a, stores necessary data in a storage device, not shown, and carries out operations necessary for medical diagnosis.

Figure 2:
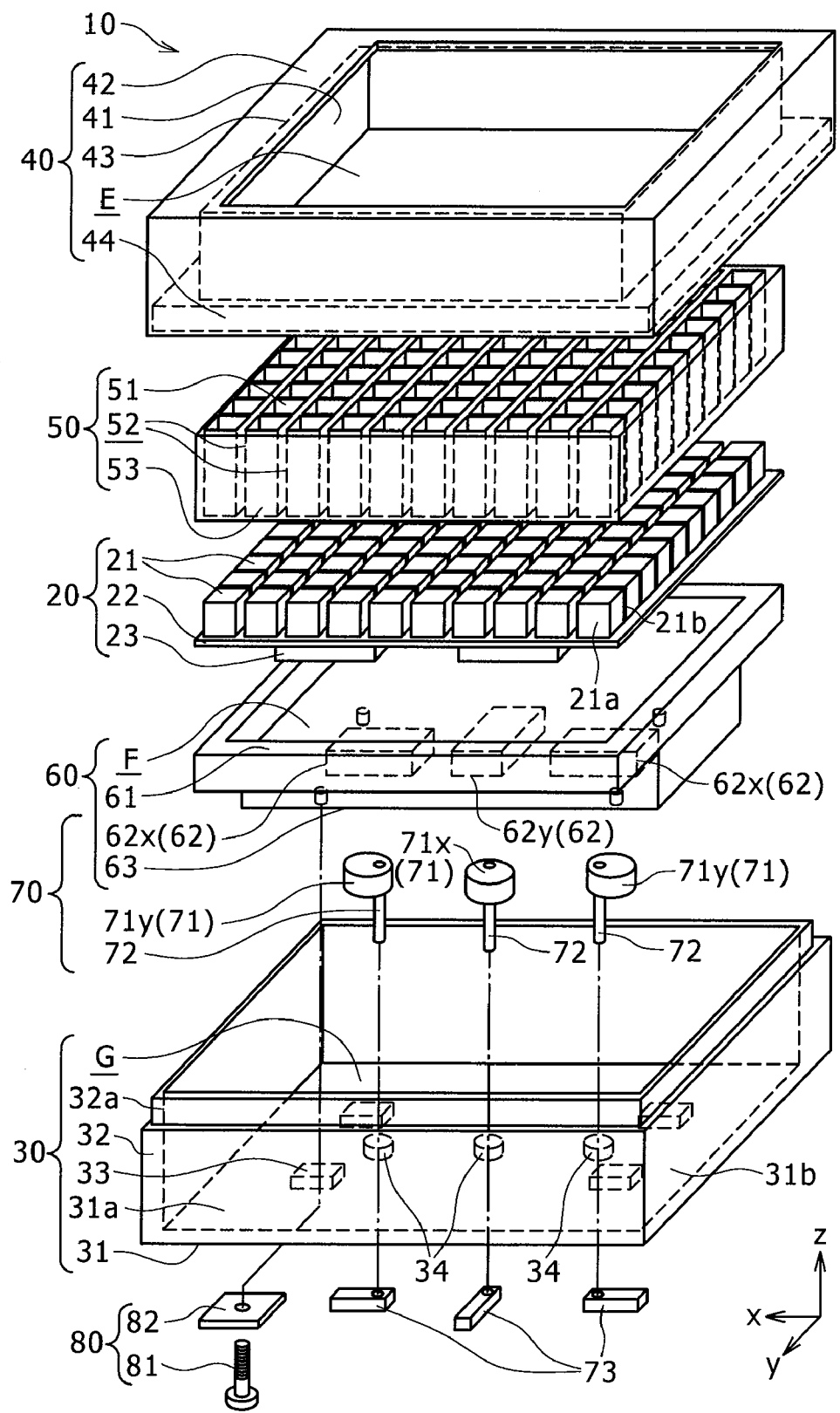
FIG. 2 is an exploded perspective view of a radiation imaging system in a preferred embodiment according to the present invention.
Figure 3A:
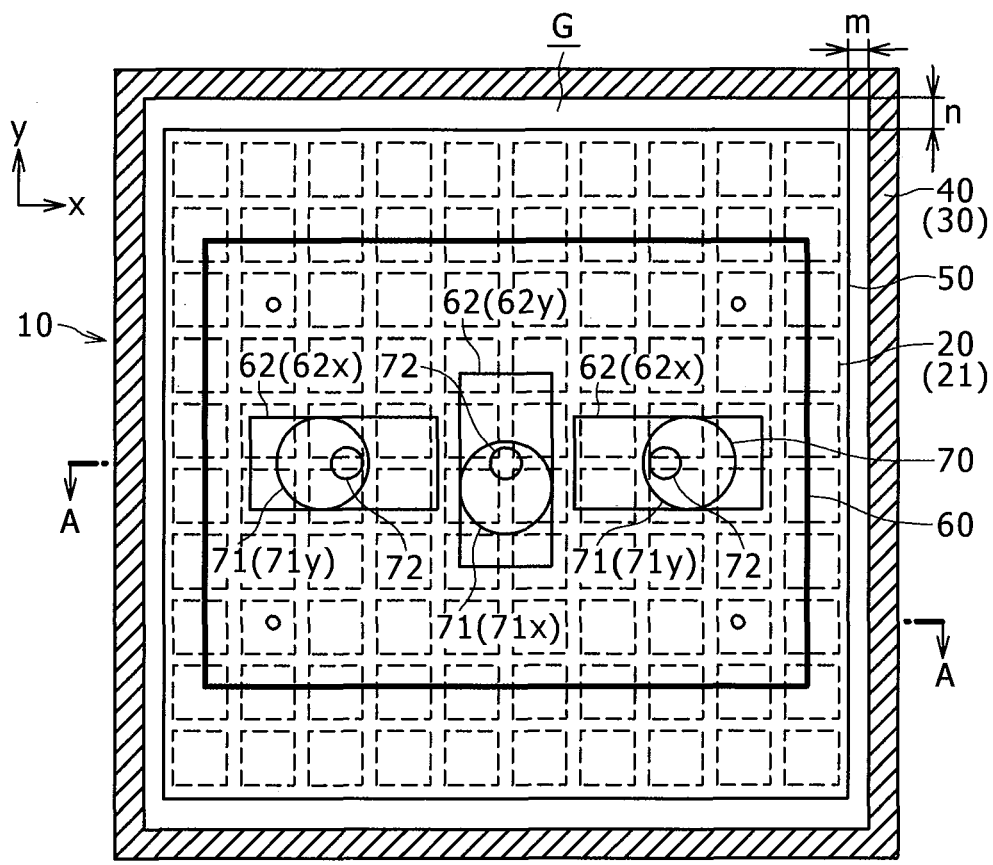
FIGS. 3A and 3B are a sectional view and a longitudinal sectional view, respectively, of the radiation imaging system shown in FIG. 2.
Figure 3B:
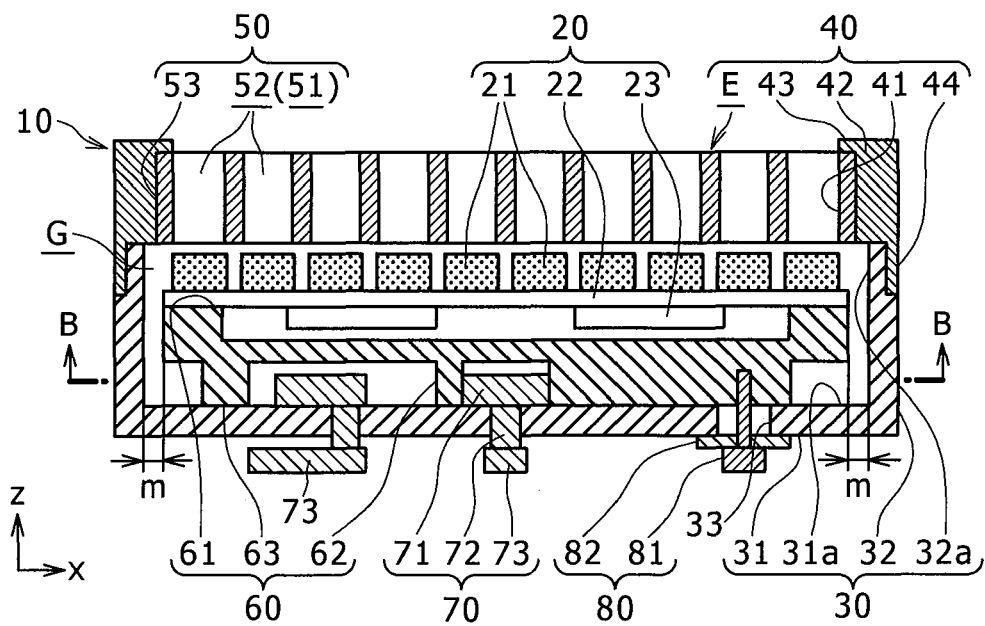

As shown in an exploded perspective view in FIG. 2, in a sectional view in FIG. 3A and a longitudinal sectional view in FIG. 3B, the radiation imaging system 10 includes a detecting unit 20 for detecting radiation, a second case 30 supported on the gantry 2 as shown in FIG. 1, a first case 40, a collimator 50 fixedly held in the first case 40, a holding case 60 holding the detecting unit 20 and fixedly held in the second case 30, and a position adjusting mechanism 70 for adjusting the positional relation between the holding case 60 and the second case 30.

The radiation imaging system 10 obtains measured data on the distribution of intensities of radioactive rays emitted by the subject 6 and fallen on the entrance surface 51 and gives the measure data to the image processing system 8 shown in FIG. 1.

The detecting unit 20 includes a substrate 22, a plurality of radiation detecting elements 21 arranged on one of the surfaces of the substrate 22, and a signal processing device 23 placed on a reflecting surface of the substrate 22. The radiation detecting elements 21 of the detecting unit 20 serve as unit pixels, respectively, to determine the distribution of intensities of the radioactive rays emitted by the subject 6 and fallen thereon. FIG. 2 shows one hundred radiation detecting elements 21 arranged in ten rows and ten columns in a conceptual picture. Actually, the detecting unit 20 is provided with several tens to several hundreds of thousands of pixels. The detecting unit 20 provided with a greater number of pixels can exhibit higher resolution in closer imaging.

The detecting element 21 measures the energy intensity of radiation fallen thereon. Since the plurality of radiation detecting elements 21 are arranged on the surface of the substrate 22, the intrasurface distribution of intensities of the incident radiation can be determined.

Each of the radiation detecting elements 21 is, for example, a semiconductor radiation detector using a CdTe semiconductor and provided with electrodes 21a and 21b on its side surfaces, respectively. The detecting element 21 converts the energy of radiation fallen thereon into corresponding electric energy and gives an electric signal representing the electric energy through the electrodes 21a and 21b to the signal processing device 23 placed on the back surface of the substrate 23

The signal processing device 23 includes an ASIC (application specified integrated circuit) and a FPGA (field programmable gate array). The signal processing device 23 detects a very weak analog signal electronically provided by the detecting element 21 and sends detection data on the wave height of the analog signal, time of detection and information about the position of the detecting element 21, namely, a signal conveying the coordinates of the position in the xy-coordinate system, to the data processing unit 9b (FIG. 1).

FIG. 5 shows possible detecting units 20.

Figure 5A:
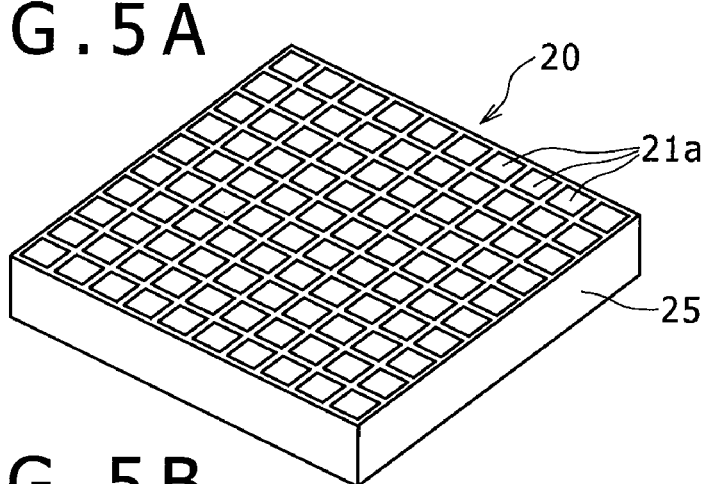
FIGS. 5A, 5B, 5C and 5D are perspective views of detecting units that can be employed by the present invention.

The detecting unit 20 shown in FIG. 5A includes a CdTe semiconductor substrate 25, a plurality of electrodes 21a arranged on the entrance surface of the CdTe semiconductor substrate 25, and electrodes, not shown, arranged on the back surface opposite the entrance surface of the CdTe semiconductor substrate 25. The area of the one electrode 21a is equal to that of one pixel.

Figure 5B:
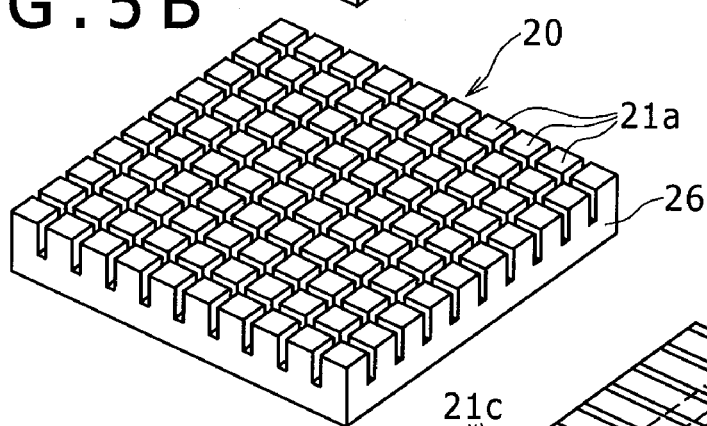

The detecting unit 20 shown in FIG. 5B includes a CdTe semiconductor substrate 25 and a plurality of electrodes 21a. Grooves are formed in the boundaries each between the adjacent electrodes 21a by dicing to demarcate the pixels. Thus the pixels on the CdTe semiconductor substrate 25 are demarcated by the grooves to form a semiconductor substrate 26 provided with the demarcated pixels.

Figure 5C:
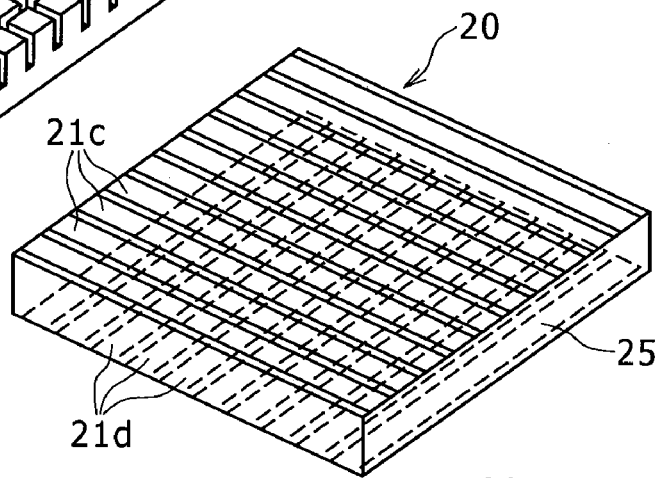

The detecting unit 20 shown in FIG. 5C includes a CdTe semiconductor substrate 25, a plurality of parallel, strip-shaped electrodes 21c formed on one of the surface of the CdTe semiconductor substrate 25, and a plurality of parallel, strip-shaped electrodes 21d formed on the other surface of the CdTe semiconductor substrate 25 so as to extend perpendicularly to the electrodes 21c. Pixels are formed at the intersections of the electrodes 21c and 21d, respectively.

Figure 5D:
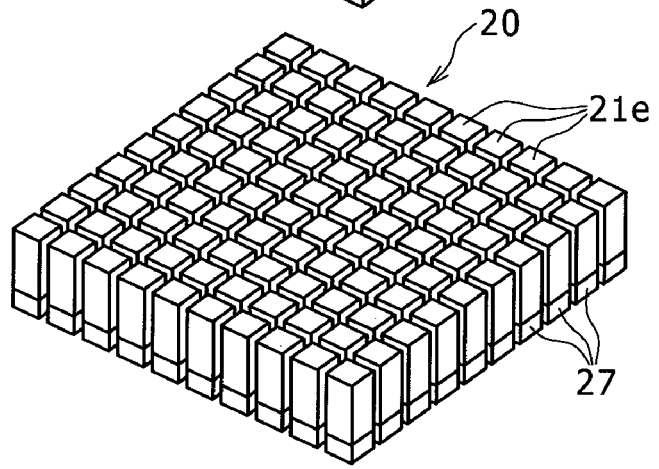

The detecting unit 20 shown in FIG. 5D includes scintillators 21e as pixels, and photodiodes 27 combined with the scintillators 213, respectively. The side surfaces of the scintillators 21e are coated with a shading material. Another detecting unit including scintillators may be provided with a PSPMT (position-sensitive photomultiplier tube) combined with the scintillators.

Referring again to FIG. 2, the collimator 50 has an entrance surface 51 on which radiation falls. The collimator 50 is provided with through holes 52 arranged so as to coincide with the radiation detecting elements 21, respectively, opening in the entrance surface 51 and extending in the direction of the thickness of the collimator 50. Radiations emitted by the subject 6 and falling only from a direction perpendicular to the entrance surface 51 can fall on the radiation detecting elements 21.

The square shape of the openings of the through holes 52 of the collimator 50 and the square shape of the surfaces of the radiation detecting elements 21 are the same. Pitches of the radiation detecting elements 21 with respect to directions along the X-axis and the Y-axis are equal to those of the through holes 52 with respect to directions along the X-axis and the Y-axis. Therefore, when the collimator 50 and the detecting unit 20 are positioned accurately relative to each other, the centers of the through holes 52 coincide with the centers of the radiation detecting elements 21, respectively.

When the collimator 50 and the detecting unit 20 are fixed relative to each other with the through holes 52 and the radiation detecting elements 21 accurately aligned, respectively, any moiré pattern will not be produced in a projected picture, and special resolution and the linearity of a picture will be improved.

When the collimator 50 is small and has a size of 100 mm sq. or below, the collimator 50 can be accurately formed by, for example, subjecting a tungsten plate or the like to an etching process or the like even if the radiation detecting elements 21 are as small as 1 to 2 mm sq.

When the collimator 50 is large and has a size above 100 mm sq., the collimator 50 cannot be necessarily formed by the foregoing fabricating method because of cost and strength and the collimator 50 may be made of an inexpensive material, such as lead.

The first case 40 has the shape of a frame forming an entrance window E surrounding the entrance surface 51 of the collimator 50. The first case 40 has an inside surface 41, an end surface 42, a retaining part 43, and a joining part 44. The first case 40 is fixed to the side surface 53 of the collimator 53. The second case 30 is joined to the first case 40 to hold the collimator 50 rigidly.

As shown in FIG. 3B, the inside surface 41 of the first case 40 is in close contact with the side surface 53 of the collimator 50 to restrain the collimator 50 from movement.

Desirably, the end surface 42 is formed in the smallest possible area that can ensure mechanical rigidity such that the radiation imaging system 10 has the largest possible effective field of view for detecting radiation falling on the XY-plane on the radiation imaging system 10.

The retaining part 43 extends from the end surface 42 into the entrance window E. The retaining part 43 restrains the collimator 50 fixed to the first case 40 from coming off from the first case 40 in the direction of the Z-axis.

The joining part 44 engages with a joining part 32a of the second case 30 formed by thinning an edge part of the side wall 32 of the second case 30 when the first case 40 and the second case 30 are joined together.

Referring again to FIG. 2, the second case 30 has a chamber G for holding the detecting unit 20 and the holding case 60 for holding the bottom wall 31, a side wall 32, adjusting openings 33, and through holes 34. As shown in FIG. 3B, the second case 30 is joined to the first case 40 so as to hold the collimator 50 and the detecting unit 20 rigidly. The second case 30 is supported on the gantry 2 as shown in FIG. 1 so as to move in a space defined by the XYZ-coordinate system.

Referring again to FIG. 2, the holding case 60 defines a holding chamber F having a space for receiving the signal processing device 23 of the detecting unit 20. The holding case 60 has an end surface 61, and a bottom wall 63 provided with guide grooves 62.

As shown in FIG. 3B, a peripheral part of the substrate 22 of the detecting unit 20 is seated on the end surface 61 of the holding case 60. The bottom wall 63 of the holding case 60 is slidably seated on the inside surface 31a of the bottom wall 31 of the second case 30. The detecting unit 20 is held rigidly in the holding space G of the second case 30 such that gaps m and n are formed between the detecting unit 20 and the second case 30 as shown in FIG. 3A. The gaps m and n allows the detecting unit 20 to move in directions parallel to the X-axis and the Y-axis in the holding chamber G for positional adjustment.

Referring again to FIG. 2, the position adjusting mechanism 70 includes adjusting cams 71x and 71y, which will be inclusively designated by 71 in some cases, shafts 72 attached to the adjusting cams 71, respectively, turning levers 73 attached to the shafts 72, respectively, and the bottom wall 63 provided with guide grooves 62x and 62y, which will be inclusively designated by 62 in some cases, of the holding case 60. The adjusting cams 71 are engaged in the guide grooves 62, respectively.

As shown in FIG. 3, the position adjusting mechanism 70 moves the holding case 60 in directions parallel to the entrance surface 51 relative to the second case 30 by distances within ranges corresponding to the respective widths of the gaps m and n to adjust the positional relation between the second case 30 and the holding case 60.

The grooves 62 open in the outside surface of the bottom wall 63 of the holding case 60. The guide grooves 62x extend along the x-axis, and the guide groove 62y extends along the y-axis perpendicular to the x-axis The adjusting cams 71 have a diameter smaller than the width of the guide grooves 62. The shafts 72 are attached to eccentric parts of the adjusting cams 71, respectively. The shafts 72 are rotatably supported in the through holes 34 formed in the bottom wall 31 of the second case 30, respectively.

The adjusting cams 71y are loosely engaged in the guide grooves 62x extending along the x-axis, and the adjusting cam 71x is loosely engaged in the guide groove 62x extending along the y-axis.

The levers 73 are attached to end parts projecting from the back surface of the second case 30, respectively, of the shafts 72 penetrating the bottom wall 31 of the second case 30. The positional relation between the radiation detecting elements 21 of the detecting unit 20 and the through holes 52 of the collimator 50 can be adjusted by turning the levers 73, which will be described later with reference to FIG. 4.

Referring again to FIG. 2, each of fasteners 80 includes a screw 81 and a washer 82. The fasteners 80 fasten the detecting unit 30 to the second case 30 after the completion of positional relation adjustment. The adjusting openings 33 formed in the bottom wall 31 to pass the screws 81 therethrough need to be formed in a size considerably greater than the diameter of the screws 81, taking adjusting allowance into consideration. When the screws 81 are fastened, the washers 82 are deformed elastically to press the bottom wall 63 of the holding case 60 against the inside surface 31a of the bottom wall 31 of the second case 30 by their resilience to maintain the correctly adjusted positional relation.

Although not shown in the drawings, a radiation shielding sheet of, for example, iron or lead is attached to inside or the outside surface of the radiation imaging system 10 to shield the detecting unit 20 from radiations other than those that pass through the through holes 52 of the collimator 50, and electromagnetic waves. The entrance surface 51 of the collimator 50 is coated with a metal plate that transmits γ-rays and stops light and electromagnetic waves, such as an aluminum plate.

Although the entrance surface 51 shown in the drawings is flat, the entrance surface 51 may be a curved surface. When the entrance surface 51 is a curved surface, the bottom wall 63 of the holding case 60 and the inside surface 31a of the bottom wall 31 of the second case 30 are curved so as to correspond to the curved entrance surface 51 so that the radiation detecting elements 21 may not be locally displaced relative to the corresponding through holes 52.

In the position adjusting mechanism 70 shown herein, the eccentric adjusting cams 71 are turned by operating the levers 73 placed on the back surface of the second case 30. The eccentric adjusting cams 71 may be automatically turned through an angle respectively by stepping motors. The adjusting cams 71 may be omitted and the detecting unit 20 fixedly mounted on an XY-stage may be automatically moved on the inside surface 31a of the bottom wall 31 of the second case 30.

When the positional adjustment can be achieved by automatically moving the detecting unit 20, the operator of the nuclear medicine diagnosis instrument 1 can adjust the position of the detecting unit 20 relative to the collimator 50, watching a picture displayed on the display 9a (FIG. 1) or the nuclear medicine diagnosis instrument 1 can automatically carry out a position adjusting operation by controlling the position adjusting mechanism 70 so that a moiré pattern produced in a picture displayed on the display 91 may be eliminated.

FIG. 4 is a view of assistance in explaining a position adjusting method using the position adjusting mechanism 70 (FIG. 2).

Figure 4A:
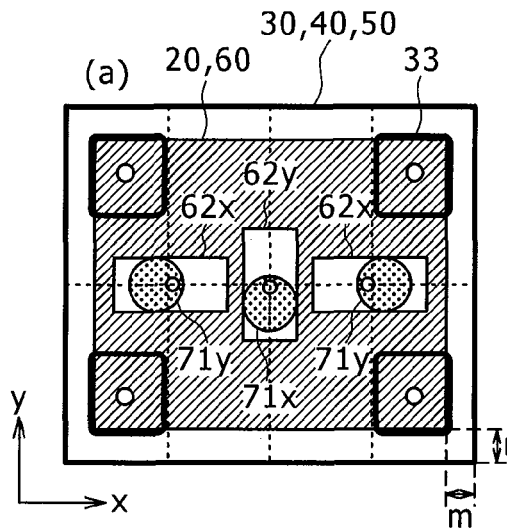
FIGS. 4A, 4B, 4C, 4D, 4E and 4F are plan views of assistance in explaining the adjustment of the positional relation between a detecting unit and a collimator in a state where the detecting unit at its home position, a state where the detecting unit has been displaced in a direction along an x-axis, in a state where the detecting unit has been displaced in a direction along a y-axis, in a state where the detecting unit has been displaced in an xy-plane, in a state where the detecting unit has been turned in a turning direction θ and in a state where the detecting unit has been displaced in the xy-plane and turned in the turning direction θ, respectively.

In FIG. 4A, the adjusting cams 71x and 71y and the holding case 60 holding the detecting unit 20 are at their home positions, respectively. When only the adjusting cam 71x is turned from the home position through an angle of 90°, the holding case 60 is guided for movement by the adjusting cams 71y engaged in the guide grooves 62x to move the detecting unit 20 in a direction parallel to the x-axis as shown in FIG. 4B.

Figure 4B:
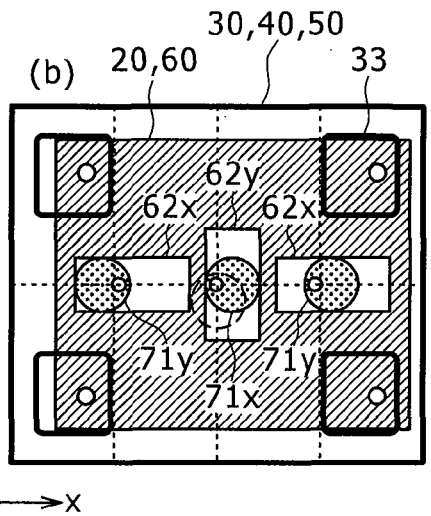
Figure 4C:
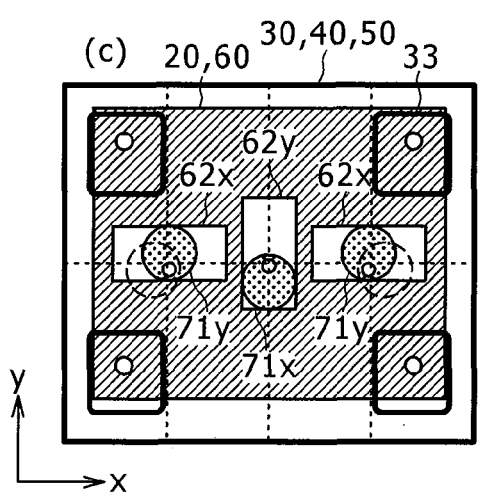

When the adjusting cams 71y are turned from their home positions shown in FIG. 4A through 90° in opposite directions, respectively, the holding case 60 is guided for movement by the adjusting cam 71x engaged in the guide groove 62y to move the detecting unit 20 in a direction parallel to the y-axis as shown in FIG. 4C.

Figure 4D:
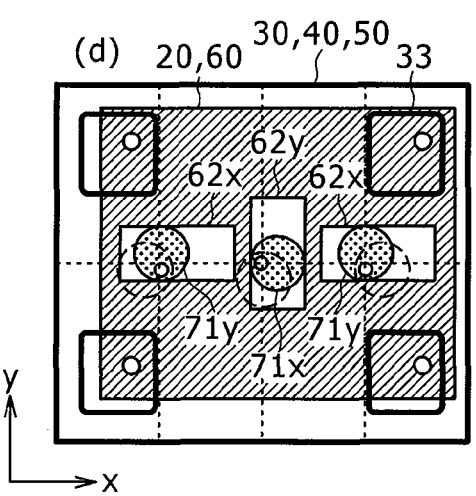

When operations for turning the adjusting cams 71x and 71y to move the holding case 60 as mentioned in connection with FIGS. 4B and 4C are executed simultaneously or successively, the detecting unit 20 is moved diagonally in the xy-plane to a position shown in FIG. 4D.

Figure 4E:
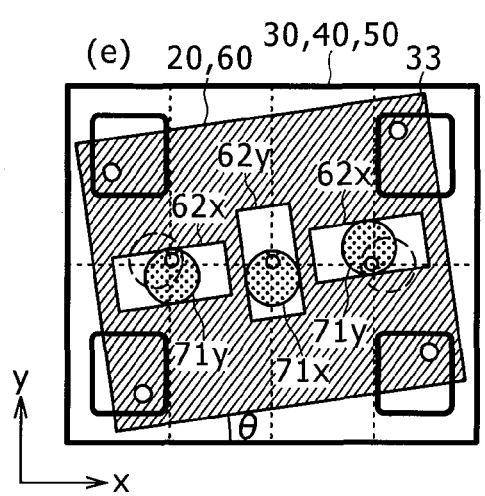

When the adjusting cams 71y are turned from their home positions shown in FIG. 4A through 90° in the same direction, the detecting unit 20 is turned in the turning direction θ to a position shown in FIG. 4E.

Figure 4F:
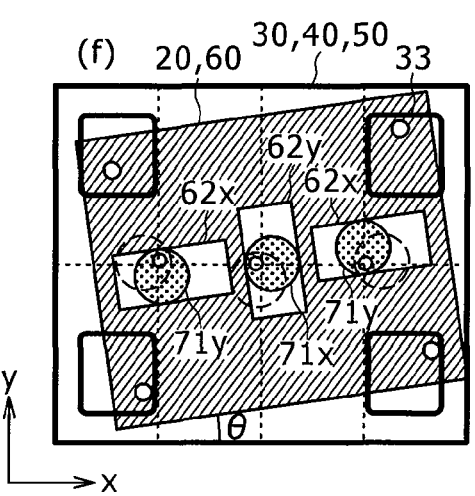

When the operations for shifting the detecting unit 20 to the position shown in FIG. 4E and an operation for turning the adjusting cam 71x are executed simultaneously or successively, the detecting unit 20 is turned in the turning direction θ and translated diagonally in the xy-plane to a position shown in FIG. 4F.

Thus, the positional relation between the detecting unit 20 and the collimator 50 can be properly adjusted by properly turning the adjusting cams 71x and 71y. Consequently, a moiré pattern is eliminated and a picture excellent in spatial resolution and linearity can be displayed.

Thus, the assembly of the detecting unit 20 and the holding case 60 can be shifted by a distance in a range limited by the gaps m and n and can be turned in the xy-plane relative to the assembly of the first case 40 and the second case 30.

The accurate positional adjustment of the detecting unit 20 relative to the collimator 50 can be surely achieved when the range in which the assembly of the detecting unit 20 and the holding case 60 can be shifted relative to the assembly of the first case 40 and the second case 30 is equal to the pitch at which the radiation detecting elements 21 (FIG. 2) or the through holes 52 are arranged. Therefore, a distance equal to the pitch at which the pixels are arranged is sufficient as the eccentricity of each of the adjusting cams, namely, the distance of the geometric center of the adjusting cam 71 from the axis of rotation of the shaft 72.

The radiation imaging system 10 and the nuclear medicine diagnosis instrument 1 described herein have the following effects.

The radiation imaging system mentioned in JP-A 2001-324569 needs a large, heavy, movable mechanism for moving the heavy collimator for position adjustment and hence a space surrounding the effective field of view of radiation, namely, the entrance surface, increases inevitably.

According to the present invention, the space surrounding the effective field of view of radiation, namely, the entrance surface, may be small because the position adjusting mechanism 70 is disposed on the back surface of the radiation imaging system 10.

The conventional SPECT (single photon emission computed tomography) system touches the subject's shoulder in obtaining an image of, for example, the head. Therefore, the radius of the revolution path needs inevitably to be greater than shoulder length. Consequently, the radiation imaging system 10 cannot be disposed close to the subject's head for imaging. The radiation imaging system of the present invention can be brought close to the head and can be made to revolve around the head without being interfered with by the shoulders and can obtain a high-definition image.

The conventional radiation imaging system needs to revolve along a revolution path of a big diameter to avoid interference with the arms in obtaining an image of the heart. The radiation imaging system 10 of the present invention can be disposed close to the body for imaging.

The radiation imaging system 10 can be brought close to a desired part of the body avoiding touching the arm or the chin in obtaining images of the sentinel lymph duct in an axillar region, the parathyroid gland and the breast to improve the accuracy of diagnosis.

The application of the radiation imaging system 10 of the present invention is not limited to a large gamma camera for a SPECT system and the radiation imaging system 10 is applicable not only to a small, portable gamma camera, but also to the position adjusting mechanisms of other radiation imaging systems, such as x-ray CT systems provided with radiation detecting elements and a collimator similar to those of the radiation imaging system 10.

The SPECT system 1 (FIG. 1) described herein as an example of the nuclear medicine diagnosis instrument is only an example. In another possible nuclear medicine diagnosis instrument according to the present invention, the radiation imaging system 10 may be suspended from the ceiling of the room or held on the wall of the room so as to be optionally movable in the XYZ-space instead of being supported on the gantry 2 and being moved along the revolution path 2a.

The application of the radiation imaging system 10 is not limited to the foregoing medical apparatus. The radiation imaging system 10 is applicable to, for example, a camera that detects radiation passed through an object of inspection for the nondestructive inspection of architectural structures.

Although the invention has been described in its preferred form with a certain degree of particularity, obviously many changes and variations are possible therein. It is therefore to be understood that the present invention may be practiced otherwise than as specifically described herein without departing from the scope and spirit thereof.

What is claimed is:

1. A radiation imaging system comprising:
   a detecting unit including a plurality of radiation detecting elements arranged in a plane for radiation detection;
   a collimator provided with through holes respectively aligned with the radiation detecting elements and opening in an entrance surface such that radiations from a specified direction are selectively made to fall on the radiation detecting elements;
   a second case joined to a first case fixed to the side surface of the collimator to define a holding chamber;
   a holder holding the detecting unit and placed in the holding chamber such that spaces that allow the holder to be moved in a plane parallel to the entrance surface are formed between the holder and the second case; and
   a position adjusting mechanism to adjust the positional relation between the second case and the holder by moving the holder relative to the second case in distance ranges defined by the spaces.

2. The radiation imaging system according to claim 1, wherein:

the position adjusting mechanism comprises a holder bottom wall provided with guide grooves, and one or more eccentric cams;

the holder bottom wall having a sliding contact with the second case and the eccentric cams being held at the second case;

the guide grooves extending respectively in a first longitudinal direction and a second longitudinal direction perpendicular to the first longitudinal direction;

the eccentric cams being loosely engaged respectively in the guide grooves extending in the first and second longitudinal directions in the holder; and the holder is displaced in the second longitudinal direction when the eccentric cam engaged in the guide groove extending in the first longitudinal direction is turned, and the holder is displaced in the first longitudinal direction when the eccentric cam engaged in the guide groove extending in the second longitudinal direction is turned.

3. The radiation imaging system according to claim 2, wherein:

the guide grooves comprise the two guide grooves extending in the first longitudinal direction and the one guide groove extending in the second longitudinal direction.

4. The radiation imaging system according to claim 2, wherein:

a shaft is attached to each of the eccentric cams, the shaft extends through a bottom wall of the second case and means to rotate the cams is attached to an outer end of the shaft projecting from the bottom wall.

5. A nuclear medicine diagnosis instrument using the radiation imaging system set forth in claim 1 for detecting the radiation emitted by a radioactive medicine given to a subject.

* * * * *